(12) United States Patent
Rached

(10) Patent No.: US 8,142,680 B2
(45) Date of Patent: Mar. 27, 2012

(54) COMPOSITIONS THAT CAN BE USED AS REFRIGERANTS

(75) Inventor: Wissam Rached, Lyons (FR)

(73) Assignee: Arkema France, Colombes (FR)

( * ) Notice: Subject to any disclaimer, the term of this patent is extended or adjusted under 35 U.S.C. 154(b) by 150 days.

(21) Appl. No.: 12/519,280

(22) PCT Filed: Dec. 17, 2007

(86) PCT No.: PCT/FR2007/052533
§ 371 (c)(1),
(2), (4) Date: Jun. 15, 2009

(87) PCT Pub. No.: WO2008/084161
PCT Pub. Date: Jul. 17, 2008

(65) Prior Publication Data
US 2010/0044620 A1    Feb. 25, 2010

(30) Foreign Application Priority Data
Dec. 19, 2006 (FR) ...................... 06 55613

(51) Int. Cl.
*C09K 5/04*    (2006.01)

(52) U.S. Cl. .............................. 252/67; 252/68; 252/69

(58) Field of Classification Search ................ 252/67, 252/68, 69
See application file for complete search history.

(56) References Cited

U.S. PATENT DOCUMENTS

| | | |
|---|---|---|
| 3,996,153 A | 12/1976 | Heeb et al. |
| 4,448,031 A | 5/1984 | Rojey et al. |
| 5,716,549 A | 2/1998 | Nimitz et al. |
| 5,826,436 A | 10/1998 | Scaringa et al. |
| 6,073,454 A | 6/2000 | Spauschus et al. |
| 6,261,473 B1 | 7/2001 | Hori |
| 7,262,227 B2 * | 8/2007 | Shibanuma et al. .......... 521/130 |
| 2003/0042463 A1 | 3/2003 | Arman et al. |
| 2004/0084652 A1 | 5/2004 | Singh et al. |
| 2004/0099838 A1 | 5/2004 | Leck et al. |
| 2006/0043331 A1 | 3/2006 | Shankland et al. |

FOREIGN PATENT DOCUMENTS

EP    1491608    12/2004

* cited by examiner

*Primary Examiner* — Douglas McGinty
(74) *Attorney, Agent, or Firm* — Steven D. Boyd

(57) ABSTRACT

The invention relates to compositions that can be used as refrigerants. More specifically, the invention relates to compositions having a very low contribution to the greenhouse effect, which can be used in the cooling and production of conditioned air. The GWP of the inventive compositions is preferably at most equal to 150.

1 Claim, No Drawings

COMPOSITIONS THAT CAN BE USED AS REFRIGERANTS

FIELD OF THE INVENTION

The present invention relates to compositions that can be used as refrigerant fluids. The invention more particularly relates to compositions whose contribution to the greenhouse effect is very low, which may be used in refrigeration and the production of conditioned air.

BACKGROUND OF THE INVENTION

The problems posed by substances that deplete the atmospheric ozone layer were addressed at Montreal, where the protocol was signed imposing a reduction in the production and use of chlorofluorocarbons (CFC). This protocol underwent amendments which imposed the phasing out of CFCs and extended the regulation to other products, including hydrochlorofluorocarbons (HCFC).

The refrigeration and conditioned-air production industry has invested greatly in the replacement of these refrigerant fluids, and hydrofluorocarbons (HFC) have accordingly been marketed.

In the motor vehicle industry, the air-conditioning systems of vehicles marketed in many countries swapped from a chlorofluorocarbon refrigerant fluid (CFC-12) to a hydrofluorocarbon refrigerant fluid (1,1,1,2-tetrafluoroethane: HFC-134a), which is less harmful to the ozone layer. However, with regard to the objectives set by the Kyoto protocol, HFC-134a (GWP=1300) is considered as having a high warming potential. The contribution to the greenhouse effect of a fluid is quantified by the GWP (global warming potential), which summarizes the warming potential, taking a reference value of 1 for carbon dioxide.

The majority of refrigeration installations operate on the principle of the vapor compression cycle. According to this principle, a refrigerant fluid is evaporated at low pressure, by taking heat from a first surrounding medium. The vapor thus formed is then compressed by means of a compressor and then passed into a condenser in which it is converted into liquid form, giving rise to a release of heat in a second surrounding area. The liquid thus condensed then circulates in an expansion vessel, at the outlet of which it is converted into a two-phase mixture of liquid and vapor, which is finally introduced into the evaporator where the liquid is again evaporated at low pressure, which completes the cycle. In a supercritical cycle, there is no condensation, and the condenser is referred to as a cooler.

Regulating the expansion vessel allows control of the overheating at the compressor inlet and optimizes the functioning of the installation.

The yield of a compression system depends on the components, the architecture of the system, the operating conditions and the fluid. The fluids used may be pure substances or azeotropic or zeotropic mixtures. The temperature glide of a fluid is defined as being the difference in temperature between the bubble point and the dew point at constant pressure. In compression systems with a supercritical cycle, the temperature glide is considered as being the difference in temperature between the inlet and outlet of the cooler.

In a theoretical compression cycle, the phase changes (condensation/evaporation) are at constant pressure. With one-component fluids and azeotropic mixtures, the condensation and evaporation are at constant temperature. The temperature glide is then zero.

Air-conditioning units, refrigeration machines and heat-exchange pumps operate on the same principles.

Since carbon dioxide is nontoxic, nonflammable and has a very low GWP, it has been proposed as a refrigerant for air-conditioning systems as a replacement for HFC-134a. However, the use of carbon dioxide has many drawbacks, especially associated with the very high pressure of its use as a refrigerant fluid in existing devices and techniques.

The use of carbon dioxide alone in a supercritical cycle or in combination with other compounds, such as HECs, in a refrigeration system or a common heat-exchange pump may thus lead to unacceptable reductions in energy efficiency if the surrounding medium (air, water or glycol-water) does not have a temperature glide as high as that of the fluid used. The consequence is that the difference between the mean temperature of the phase change of a mixture comprising carbon dioxide and the mean temperature of the surrounding medium increases, thus resulting in an increase in the difference between the evaporation and cooling pressures, which has the direct consequence of reducing the energy efficiency of the refrigeration system or of the heat-exchange pump. This energy efficiency also decreases following the degradation of efficiency of the exchangers as a result of the variation of the difference in temperatures between the refrigerant fluid and the surrounding medium across the exchanger.

Document U.S. Pat. No. 6,073,454 discloses the use of a co-fluid in combination with carbon dioxide as a refrigerant for reducing the working pressure. However, the refrigeration performance is insufficient.

DETAILED DESCRIPTION OF THE INVENTION

Compositions that can be used as refrigerant fluids and that have a low GWP have now been found. The GWP of the compositions according to the present invention is preferably not more than 150.

The compositions according to the present invention comprise at least one compound (A) chosen from the group constituted by hydrofluorocarbons, (hydro)fluoro-olefins, (hydro)fluoroiodocarbons and hydrocarbons, at least one compound (B) chosen from the group constituted by rare gases, nitrogen, nitrogen dioxide, hydrogen sulfide and carbon dioxide, and at least one functionalized organic compound (C) with a boiling point at atmospheric pressure of greater than 60° C.

The functionalized organic compound (C) preferably has a melting point at atmospheric pressure of less than −20° C. and/or a flash point >50° C. and advantageously >10° C.

These compositions preferably comprise from 5% to 90% by weight of compound(s) (A), from 5% to 40% by weight of compound(s) (B) and from 5% to 55% by weight of compound(s) (C).

These compositions advantageously comprise from 15% to 80% by weight of compound(s) (A), from 10% to 40% by weight of compound(s) (B) and from 10% to 45% by weight of compound(s) (C).

Hydrofluorocarbons that may especially be mentioned include difluoromethane, difluoroethane, 1,1,1,2-tetrafluoroethane, 1,1,2,2-tetrafluoroethane, pentafluoroethane, pentafluoropropane, heptafluoropropane and pentafluorobutane. Difluoromethane, difluoroethane and 1,1,1,2-tetrafluoroethane are preferred.

When 1,1,1,2-tetrafluoroethane is present in the composition, it preferably represents not more than 10% of the total weight.

(Hydro)fluoroolefins that may especially be mentioned include (hydro)fluoroethylenes, (hydra)fluoropropylenes and (hydro)fluorobutylenes. (Hydro)fluoropropylenes are preferred.

(Hydro)fluoropropylenes that may especially be mentioned include difluoropropylene (HFO-1252), tri-fluoropropylene (HFO-1243), tetrafluoropropylene (HFO-1234) and pentafluoropropylene (HFO-1225). The preferred hydrofluoropropylenes are 1,3,3,3-tetra-fluoropropylene (HFO-1234ze), 2,3,3,3-tetrafluoropro-pylene (HFO-1234yf) and 1,2,3,3,3-pentafluoropropylene (HFO-1225ye), and also each of the stereoisomers thereof. Perfluoropropylene may also be suitable for use. 2,3,3,3-Tetrafluoropropylene (HFO-1234yf) is particularly preferred.

A (hydro)fluoroiodocarbon that may be mentioned is trifluoroiodomethane ($CF_3I$).

Carbon dioxide is preferably chosen as compound (B).

Functionalized organic compounds (C) that may especially be mentioned include ethylene glycol, diethylene glycol, triethylene glycol, propylene glycol, dipropylene glycol, hexylene glycol, 1,3-butanediol, diacetone alcohol, ($C_6H_{12}O_2$), diethyl carbonate, propylene carbonate, 4-methyl-1,3-dioxolan-2-one, N,N-diethylformamide, cyclohexylamine, aniline, diethylamine, 4-hydroxy-4-methylpentanone, 2-methyl-2-pentanol-4-one, 3-methoxy-3-methyl-1-butanol, methyl-diethanolamine, ethyl amine ketone, tripropylene glycol methyl ether, dipropylene glycol methyl ether, dipropylene glycol n-propyl ether, dipropylene glycol n-butyl ether, 5-methyl-3-heptanone, dimethyl sulfoxide, dimethyl sulfone, dibenzyl ester, dimethyl adipate, dimethyl glutarate, dimethyl succinate, diisobutyl adipate, glyceryl carbonate, γ-butyrolactone, 1,3-benzenediol, trimethyl phosphate, polyoxymethylenes, 1-ethylpyrrolidin-2-one, 1-methyl-2-pyrrolidone, dipropylene glycol methyl ether acetate, 5-methyl-2-propan-2-ylcyclohexan-1-ol, dimethyl isosorbide, nonafluorobutyl ethyl ether ($C_4F_9OC_2H_5$), 2-ethylhexyl acetate, ethyl benzoate, ethylene glycol diacetate, ethyl malonate, bis(2-butoxyethyl)ether, dibutyl sulfide, glyceryl triacetate, ethylene glycol monomethyl ether, diethylene glycol monomethyl ether, triethylene glycol monomethyl ether, ethylene glycol dimethyl ether, diethylene glycol dimethyl ether, triethylene glycol dimethyl ether, tetraethylene glycol dimethyl ether, diethylene glycol monoethyl ether, diethylene glycol diethyl ether, ethylene glycol monobutyl ether, diethylene glycol monobutyl ether, propylene glycol methyl ether acetate, propylene glycol methyl ether propionate, ethylene glycol butyl ether acetate, diethylene glycol butyl ether acetate, dipropylene glycol methyl ether acetate, triethylene glycol monobutyl ether, polyethylene glycol dimethyl ether and ionic liquids.

The preferred compounds (C) are: propylene carbonate, dipropylene glycol n-butyl ether, tripropylene glycol methyl ether, tetraethylene glycol dimethyl ether, diethylene glycol diethyl ether, triethylene glycol monoethyl ether, triethylene glycol monobutyl ether, dipropylene glycol methyl ether acetate and ethylene glycol diacetate, perfluoro-1,3-dimethylcyclohexane, perfluorooctane, perfluoro-1,3,5-trimethylcyclohexane, perfluorotributylamine, perfluoropolyether $CF_3[(OCF(CF_3)CF_2)_m(OCF_2)_n]OCF_3$ (Galden HT 55, 70, 85, 90, 110).

The compounds (C) that are advantageously preferred are: dipropylene glycol n-butyl ether, 3-methoxy-3-methyl-1-butanol, dipropylene glycol methyl ether, dipropylene glycol propyl ether, dipropylene glycol methyl ether acetate, ethyl diglycol acetate, diethylene glycol butyl ether, 2-ethylhexyl acetate, tetraethylene glycol dimethyl ether, glyceryl triacetate, 2-butoxy-2-ethoxyethyl acetate, diethyl malonate, diethylene glycol diethyl ether, dimethyl glutarate, ethyl benzoate, triethylene glycol monobutyl ether, butyl sulfide and nonafluorobutyl ethyl ether.

Examples of particularly preferred compositions that may especially be mentioned include those comprising
  difluoromethane, carbon dioxide and ethylene glycol diacetate,
  difluoroethane, carbon dioxide and ethylene glycol diacetate,
  2,3,3,3-tetrafluoropropylene (HFO-1234yf), carbon dioxide and ethylene glycol diacetate.

The compositions according to the present invention are suitable for compression systems, for cooling applications (refrigeration system) or heating applications (heat-exchange pump) or in reversible machines, which produce cold for cooling or heat for heating.

With the compositions of the present invention, the presence of a liquid phase inside exchangers, comprising compound (C), and of a gas phase promotes the dissolution and evaporation phenomena according to the pressure levels. In the condenser, with an increase in pressure, the more volatile compounds, such as carbon dioxide, dissolve in the liquid phase and it is the heat of dissolution that adds to the heat of condensation. With the drop in pressure at the evaporator, the more volatile compounds are released from the liquid phase and absorb heat from the external medium. This absorbed heat adds to the heat of evaporation of the less volatile compounds (A) and thus increases the cooling power and the performance of the system. The compositions according to the present invention also have, according to the nature of the component (C), the advantage of functioning with a reduced amount of lubricants or in the absence of lubricant when they are used in compressors.

A subject of the present invention is also the use of the compositions described above as energy-transfer fluids and refrigerant fluids, in particular in the production of conditioned air.

The compositions described above are particularly suitable for use as refrigerant fluids in the air conditioning of vehicles and can partially or totally replace 1,1,1,2-tetrafluoroethane.

EXPERIMENTAL SECTION

A) Absorption of $CO_2$ 64 q of carbon dioxide are introduced into a 320 ml autoclave equipped with a temperature sensor, a pressure sensor and a magnetic stirrer. The functionalized organic compound is then gradually introduced therein using a volume-displacement pump. The temperature of the autoclave is maintained at 40° C., using a thermostatically maintained bath, throughout the tests.

The pressure of the resulting mixture is given in Table 1.

TABLE 1

| % of the functionalized organic compound (vol/vol) | 0 | 7 | 15 | 22 | 30 | 37 |
|---|---|---|---|---|---|---|
| | | | Pressure (bar) | | | |
| Glyceryl carbonate | 73.38 | 74.76 | 76.31 | 77.87 | 79.47 | 81.38 |
| Dipropylene glycol n-butyl ether | 72.6 | 67.7 | 63.25 | 59.49 | 56.32 | 53.15 |
| Dipropylene glycol | 70.56 | 70.55 | 70.39 | 70.16 | 70.09 | 69.75 |
| 3-Methoxy-3-methyl-1-butanol | 72.58 | 67.71 | 64.71 | 62.79 | 59.92 | 57.29 |

TABLE 1-continued

| % of the functionalized organic compound (vol/vol) | 0 | 7 | 15 | 22 | 30 | 37 |
|---|---|---|---|---|---|---|
| | | | Pressure (bar) | | | |
| Dipropylene glycol methyl ether | 73.35 | 67.15 | 62.74 | 59.06 | 55.95 | 53.26 |
| Dipropylene glycol propyl ether | 72.53 | 68 | 63.96 | 60.5 | 57.54 | 54.79 |
| Tripropylene glycol methyl ether | 75.35 | 70.71 | 66.95 | 63.87 | 61.23 | 59.4 |
| Tributyl borate | 69.59 | 66.64 | 65.4 | 64.84 | 63 | 61.32 |
| Dipropylene glycol methyl ether acetate | 72.51 | 64.89 | 58.92 | 54.17 | 50.16 | 46.82 |
| Ethyl diglycol acetate | 72.04 | 65.79 | 60.77 | 56.3 | 52.28 | 49.24 |
| Diethylene glycol dibutyl ether | 71.61 | 66.96 | 64.86 | 62.19 | 59.03 | 56.41 |
| 2-Ethylhexyl acetate | 72.72 | 66.36 | 61.49 | 57.51 | 54.24 | 51.36 |
| Tetraethylene glycol dimethyl ether | 71.79 | 65.64 | 62.66 | 58.17 | 54.32 | 50.99 |
| Ethylene glycol diacetate | 72.49 | 63.11 | 56.14 | 50.8 | 46.55 | 43.17 |
| Glyceryl triacetate | 72.44 | 67.14 | 61.42 | 56.69 | 52.58 | 49.24 |
| 2-Butoxy-2-ethoxyethyl acetate | 71.79 | 66.25 | 61.57 | 57.09 | 53.2 | 49.87 |
| Diethyl malonate | 69.88 | 62.16 | 56.46 | 51.46 | 47.52 | 44.28 |
| Diethylene glycol diethyl ether | 71.82 | 64.57 | 58.47 | 53.65 | 49.53 | 46.03 |
| Dimethyl glutarate | 63.49 | 55.22 | 49.13 | 44.43 | 40.75 | 37.81 |
| Ethyl benzoate | 73.45 | 68.49 | 64.69 | 61.36 | 58.49 | 56.08 |
| Triethylene glycol monobutyl ether | 71.61 | 69.46 | 68.13 | 66.55 | 64.6 | 62.51 |
| Butyl sulfide | 72.45 | 68.48 | 66.05 | 63.45 | 61.16 | 59.2 |
| Nonafluorobutyl ethyl ether | 70.98 | 61.96 | 55.53 | 50.87 | 47.12 | 44.15 |

B) Thermodynamic Performance

Table 2 gives the performance of a composition comprising carbon dioxide (R744), ethylene glycol diacetate (EGDA) and optionally difluoromethane (R32). The thermodynamic properties used to calculate the performance may be summarized as follows:

The PSRK predictive model (T. Holderbaum and J. Gmehling, "A group contribution equation of state based on UNIFAC", *Fluid Phase Equilibrium*, 1991, 70, 251-265) was used to calculate the "liquid-vapor" equilibria according to a symmetry approach and based on the group contribution methods. It is composed of an equation of state, an alpha function, a mixing rule and a UNIFAC solution model (A. Fredenslund, R. L. Jones and J. M. Prausnitz, "Group contribution estimation of activity coefficients in non-ideal liquid mixtures", *AIChE J.*, 1975, 21, 1086-1099).

The parameters of each of the constituents (carbon dioxide, difluoromethane and ethylene glycol diacetate) come from the Dortmund Data Bank (DDB) database (www.ddbst.de).

The binary systems and then the ternary systems were studied.

The PSRK UNIFAC parameters for the carbon dioxide and ethylene glycol diacetate binary are available in the Dortmund Data Bank (DDB) database (www.ddbst.de).

As regards the difluoromethane and carbon dioxide binary system, the available data were used (F. Rivollet, A. Chapoy, C. Coquelet and D. Richon, *Fluid Phase Equilibrium*, 218, 2004, 95-101, and R. A. Adams and F. P. Stein, *J. Chem. Eng. Data*, 16, (1971), 146-149).

As no literature data were available, measurements were taken for the difluoromethane and ethylene glycol diacetate binary system using the variable-volume synthetic technique (M. Meskel-Lesavre, D. Richon and H. Renon, *Ind. Eng. Chem. Fundam.*, 20, 1981, 284-289).

Using the PSRK model and the parameters obtained from the binary systems, the bubble point corresponding to three ternary mixtures (carbon dioxide, difluoromethane and ethylene glycol diacetate) was predicted, and these predictions were validated with values measured using the variable-volume synthetic technique.

The equations of state developed for the ternary mixture are then used to determine the temperature-pressure curve and the performance in a theoretical compression cycle.

The conditions are:

external temperature 35° C.

internal temperature 5° C.

no loss of pressure in the exchangers isotropic compression cooling to 0° C. at the condenser outlet internal exchanger: cooling to 25° C.

vapor titer at the evaporator outlet: 0.5 mol/mol $P_{evap}$ denotes the evaporation pressure (kPa), $P_{cond}$ denotes the condensation pressure (kPa), $T_{comp\ outlet}$ denotes the temperature at the compressor outlet (° C.), COP denotes the coefficient of performance and CAP denotes the volumetric capacity ($kJ/m^3$).

TABLE 2

| R744 weight % | EGDA weight % | $P_{evap}$ (kPa) | $P_{cond}$ (kPa) | $T_{comp\ outlet}$ (° C.) | COP | CAP ($kJ/m^3$) |
|---|---|---|---|---|---|---|
| 60 | 40 | 2449 | 5895 | 97 | 2.20 | 8197.24 |
| 50 | 50 | 1908 | 5160 | 110 | 1.88 | 6327.27 |
| 40 | 60 | 1288 | 4382 | 133 | 1.49 | 4257.64 |
| 30 | 70 | 568 | 3529 | 202 | 0.92 | 1867.87 |

| R744 weight % | EGDA weight % | R32 weight % | $P_{evap}$ (kPa) | $P_{cond}$ (kPa) | $T_{comp\ outlet}$ (° C.) | COP | CAP ($kJ/m^3$) |
|---|---|---|---|---|---|---|---|
| 35 | 35 | 30 | 1392 | 4094 | 112.9 | 2.23 | 5757.66 |
| 30 | 30 | 40 | 1293 | 3788 | 110 | 2.42 | 5699.30 |
| 25 | 25 | 50 | 1214 | 3498 | 106 | 2.64 | 5687.62 |
| 20 | 20 | 60 | 1147 | 3220 | 101 | 2.90 | 5700.29 |
| 40 | 27 | 33 | 1640 | 4477 | 105 | 2.45 | 6847.71 |

TABLE 2-continued

| | | | | | | | |
|---|---|---|---|---|---|---|---|
| 35 | 23 | 42 | 1513 | 4162 | 104 | 2.60 | 6686.71 |
| 30 | 20 | 50 | 1395 | 3854 | 102.9 | 2.73 | 6488.47 |
| 25 | 17 | 58 | 1293 | 3556 | 100 | 2.90 | 6292.26 |
| 20 | 13 | 67 | 1211 | 3275 | 97 | 3.12 | 6185.94 |
| 10 | 7 | 83 | 1058 | 2721 | 90 | 3.64 | 5888.68 |
| 40 | 13 | 47 | 1746 | 4509 | 97 | 2.85 | 7914.97 |
| 35 | 12 | 53 | 1602 | 4200 | 98 | 2.93 | 7504.62 |
| 30 | 10 | 60 | 1478 | 3900 | 97 | 3.03 | 7189.41 |
| 25 | 8 | 67 | 1366 | 3609 | 95 | 3.17 | 6894.49 |
| 20 | 7 | 73 | 1258 | 3318 | 94 | 3.29 | 6589.8 |

The invention claimed is:

1. A composition comprising 30% to 80% by weight of difluoromethane, 10% to 30% by weight carbon dioxide, and 20% to 35% by weight ethylene glycol diacetate, said ethylene glycol diacetate having a boiling point at atmospheric pressure of greater than 60° C. a melting point at atmospheric pressure<−20° C. and/or a flash point>70° C.

* * * * *